United States Patent [19]

Holmbo

[11] 4,398,537
[45] Aug. 16, 1983

[54] INDEPENDENTLY RATE-ADJUSTING MULTIPLE CHANNEL CONTROLLER FOR NERVE STIMULATOR TRANSMITTER

[75] Inventor: Dwight N. Holmbo, Prior Lake, Minn.

[73] Assignee: Medtronic, Inc., Minneapolis, Minn.

[21] Appl. No.: 226,393

[22] Filed: Jan. 19, 1981

[51] Int. Cl.³ .............................................. A61N 1/36
[52] U.S. Cl. ................................................ 128/420 R
[58] Field of Search ............... 128/420 R, 422, 423 R, 128/421

[56] References Cited

U.S. PATENT DOCUMENTS

| | | | |
|---|---|---|---|
| 3,718,132 | 2/1973 | Holt et al. | 128/421 |
| 3,774,620 | 11/1973 | Hansjurgens | 128/420 A |
| 3,888,261 | 6/1975 | Maurer | 128/420 R |
| 3,893,463 | 8/1975 | Williams | 128/421 |

Primary Examiner—William E. Kamm
Attorney, Agent, or Firm—Merchant, Gould, Smith, Edell, Welter & Schmidt

[57] ABSTRACT

An independently rate-adjustable multiple channel controller-transmitter for a nerve stimulator to be used in conjunction with an implanted stimulation pulse output unit includes a rate generating circuit (40,41,43,44) for producing asynchronous trigger signals of independently adjustable rate and width, a transmitting circuit (46,47,48,49) for generating bursts of RF energy at separate frequencies in response to the trigger signals, and a rate control circuit (50) for preventing excitation of the transmitting circuit by more than one trigger signal at a time. In the event that two or more trigger signals coincide at the transmitting circuit (46,47,48,49), the rate control circuit (50) blocks and delays the latter occurring trigger signals with only minor and insignificant effect on trigger signal rate.

17 Claims, 6 Drawing Figures

D-TYPE FLIP FLOP LOGIC TABLE

| R | S | Q |
|---|---|---|
| 0 | 1 | 1 |
| 1 | 0 | 0 |
| 1 | 1 | 1 |

INDEPENDENTLY RATE-ADJUSTING MULTIPLE CHANNEL CONTROLLER FOR NERVE STIMULATOR TRANSMITTER

TECHNICAL FIELD OF THE INVENTION

The invention pertains to the field of nerve stimulators used in the field of medicine for the relief of pain. More particularly, the invention relates to an improved external controller-transmitter unit for an implantable multiple channel nerve stimulator, that permits independent adjustments of the stimulating pulse repetition rate for the multiple channels.

BACKGROUND OF THE INVENTION

Electrical nerve stimulators have become widely used in recent years in the field of medicine for the treatment of chronic intractable pain. Such devices include circuitry for generating electrical pulses, and electrode leads for delivering the pulses to the site of the pain within the body. The electrical stimulating pulses produce the effect of masking the sensation of pain, and this method is preferable to drug therapy for many types of pain, because it avoids subjecting the patient to possible dangerous side effects. In the control of chronic pain by a nerve stimulator, there are generally provided adjustments or controls so that the stimulation delivered by the device can be adjusted or controlled according to the needs of the patient, which sometimes vary from day to day, or even minute to minute. Ideally, the pulse repetition rate, the pulse amplitude and the pulse width should be controllable to provide maximum flexibility in meeting the patient's needs.

Trancutaneous stimulators are worn or carried outside the body and have electrodes secured to the skin over the affected area to apply the electrical stimulation thereto. For some types of pain in certain locations of the body such as the spine or the brain, it is preferable to have an implantable lead with electrodes at the tip that can be positioned by the physician to the location of maximum effectiveness. For long-term treatment, it is preferable that the stimulating pulse output circuits also be implanted within the body so as to avoid the necessity of an electrical lead passing through the skin to external circuitry, since the site of a lead passing through the skin would have the potential for injury or infection.

An important type of implantable nerve stimulator is designed for use with an external controller-transmitter which provides not only the control of the repetition rate, pulse width and amplitude of the stimulating pulses, but also provides the energy for the pulses, transmitted electromagnetically by RF energy through the skin to the implanted unit. This avoids either having a lead extend through the skin, or having an implanted unit that depends upon batteries which have a finite life after which they must be replaced. The controller-transmitter unit has an antenna placed on the skin for close coupling with the antenna of the implanted unit so that energy will be transmitted thereto with reasonable efficiency.

Implantable nerve stimulators of this type have been provided in the prior art. In one prior art two channel device, the controller-transmitter unit consists of pulse generators for each of the channels, and a transmitter for sending bursts of RF energy to the antenna, under control of the pulse generators. The pulse generator for one channel causes transmission of a burst at a first RF frequency, for example 185 KHz, and the pulse generator for the second channel causes transmission of a burst at a second RF frequency, for example 460 KHz. The implanted unit has filter circuits tuned to these two transmission frequencies, and the outputs from the filters connect respectively to stimulating pulse output circuits for the two channels. Leads then connect from the output circuits to the stimulating sites within the body. For example, one lead may be positioned with its electrode along a location on the spine, while the other channel lead may extend to a stimulation site at the brain. A burst of RF energy causes delivery of a stimulating pulse to the channel corresponding to the frequency of the RF burst. Typically, pulse rates range from 10 to 100 pulses per second while pulse width varies between 0.05 and 2 milliseconds.

In this prior art device, the pulse width and the pulse amplitude for each channel can be independently adjusted by circuits in the controller-transmitter unit that control the amplitude and duration of the RF bursts, respectively. The frequency or repetition rate of the stimulation pulses can also be controlled by adjustment of the pulse generators in the controller-transmitter unit. However, repetition rates of the two channels cannot independently be adjusted, but instead they must operate at the same repetition rate, with their respective pulses or bursts out of phase with each other sufficiently so that the transmitter is not required to transmit both frequencies simultaneously. Transmission of both frequencies simultaneously would result in unwanted interaction both in the transmitter and in the implanted receiver section, resulting in undefined and undesirable pulses. Attempts to provide independent rate adjustments for the two channels would result in some of the pulses to the two channels coinciding or overlapping, leading to undesirable simultaneous transmission.

However, there is a need for independent rate adjustments of the multiple channels, since the nature of the pain being treated at the two different locations within the body often requires different rates that, in general, are totally independent of one another, and the prior art implantable nerve stimulator, described above, does not permit independent rates.

SUMMARY OF THE INVENTION

The present invention provides an improved controller-transmitter unit for a multiple channel nerve stimulator, that provides independent rate adjustments for the multiple channels, while preventing unwanted mixing or interaction of the transmitted frequencies. This is accomplished by a circuit which detects potential overlaps or simultaneous output pulses from the multiple channels, and functions to suppress or delay the latter-starting pulse until after delivery of the earlier starting pulse, so as to avoid overlap of pulses at the transmitter. This permits fully independent rate adjustment of the channels, with no missed pulses or undesirable pulse interaction, and with only negligible and infrequent phase shifts of pulses.

BRIEF DESCRIPTION OF THE DRAWING

FIG. 1A is a block diagram of an alternate embodiment of the controller-transmitter of FIG. 1;

DETAILED DESCRIPTION OF THE PREFERRED EMBODIMENT

Figure 1:
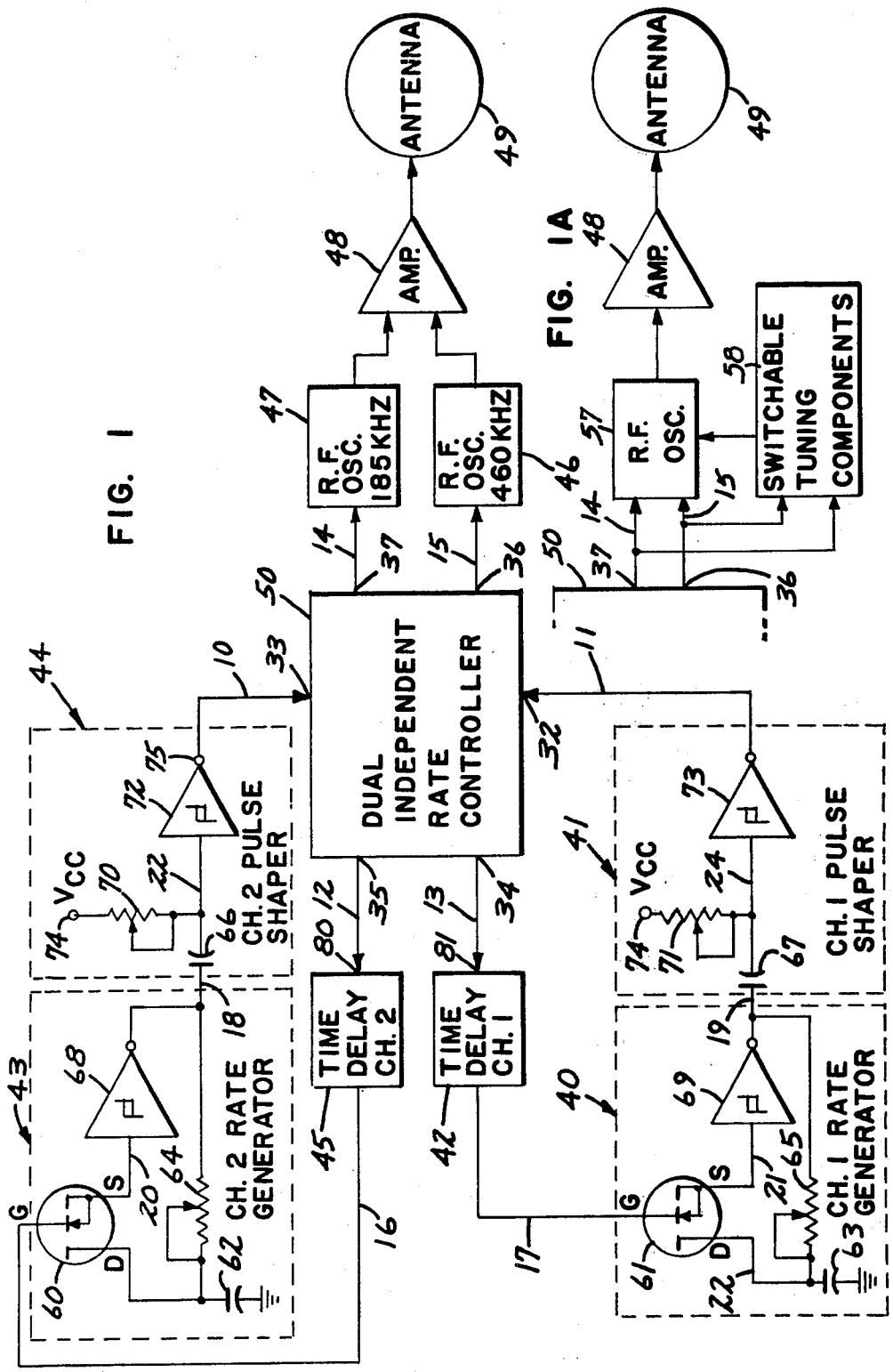
FIG. 1 is a block diagram of a controller-transmitter for a two-channel implantable nerve stimulator, incorporating the present invention.

In the present invention the dual independent rate controller, hereinafter called the controller, prevents the coincidence or overlap of asynchronous stimulation pulses in the output amplifier of the transmitter. As shown in FIG. 1, the controller 50 is utilized in a closed loop configuration. The channel 1 loop consists of rate generator 40, pulse shaper 41, controller 50, and time delay 42. The channel 2 loop is identical but independent of the channel 1 loop with corresponding elements 43, 44, 50, and 45.

Figure 2:
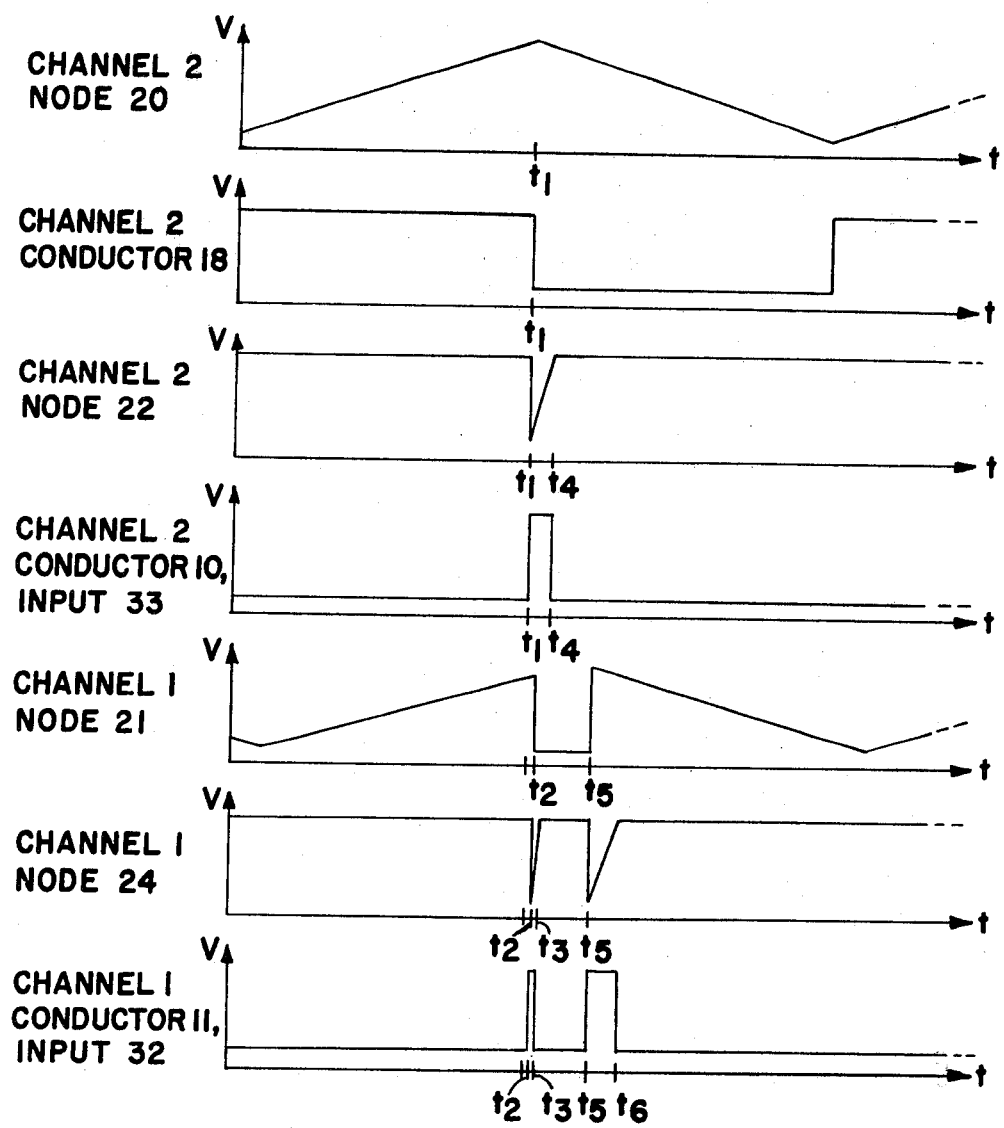
FIGS. 2 and 3 are graphs of various waveforms illustrating the operation of the controller-transmitter of FIG. 1.

Each rate generator consists of an inverting Schmitt trigger, an RC charging circuit, and a vertical field effect transistor (VFET) utilized as a high speed switch between the RC network and the input to the Schmitt trigger. Looking at channel 2 rate generator 43 for example, it will be seen that with VFET 60 switched "on" capacitor 62 will charge and discharge through adjustable resistor 64 as Schmitt trigger inverter 68 alternates states. The frequency of alteration or rate can be varied by adjusting resistor 64. Examples of waveforms present on node 20 and conductor 18 are illustrated in FIG. 2, being labeled accordingly. The corresponding channel 1 VFET, charging capacitor, and adjustable resistor are referenced respectively as 61, 63, and 65. Conductors 18 and 19 connect the output of rate generators 43 and 40 to the input of their associated pulse shapers 44 and 41.

Each pulse shaper similarly consists of a RC charging network, the output of which is connected to a Schmitt trigger inverter. As can be seen by examining channel 2 pulse shaper 44, the transition of Schmitt trigger inverter 68 to its low level output voltage cycle results in an instantaneously corresponding low voltage on node 22 which switches the Schmitt trigger inverter 72 output 75 to a high level voltage. Output 75 remains high until the voltage on the node 22 side of capacitor 66 returns to the high level input voltage threshold of said Schmitt trigger inverter 72, and thereby causing output 75 to return to a low voltage. By varying adjustable resistor 70 stimulation pulse trigger signals of differing width may be obtained at said output 75. The corresponding FIG. 2 graphs show examples of waveforms possible on node 22 and output 75 given the output from Schmitt trigger invertor 68 indicated by the graph corresponding to conductor 18.

As shown, controller 50 has two inputs 32 and 33 and four outputs 34, 35, 36, and 37. Reference 10 is a conductor connected to the controller 50 channel 2 input 33 and likewise conductor 11 is connected to channel 1 input 32. Conductors 12 and 13 connect the delay trigger outputs 35 and 34 to time delays 45 and 42 for channel 2 and channel 1, respectively. The through outputs 37 and 36 of controller 50 are connected, respectively, to oscillators 47 and 46 through conductors 14 and 15.

Time delays 45 and 42 both perform the function wherein a trigger pulse input to the respective inputs 80 and 81 produces a low level pulse of preset length at their corresponding output. The outputs of time delays 45 and 42 are connected to the corresponding gates of VFETs 60 and 61, through conductors 16 and 17 respectively.

In the described configuration, square waves of independently adjustable frequencies are output from rate generators 40 and 43, and into the respective inputs of pulse shapers 41 and 44, which may be adjusted to produce rate trigger pulses of varying width. When not coincident, these asynchronous pulses are fed through controller 50 and serve to energize their associated RF oscillator 46 or 47. The output of each oscillator is then input into a single amplifier 48 and antenna 49 transmission network. In practice RF oscillators 46 and 47 may be reduced to a single oscillator having switchable tuning components corresponding to each channel. This alternative embodiment is shown in FIG. 1A which includes a single RF oscillator 57 having switchable tuning components 58, so that its frequency can be adjusted thereby. In the alternate embodiment, the outputs 36 and 37 of dual independent rate controller 50 are applied both to RF oscillator 57, and also to the switchable tuning components 58. The output of oscillator 57 goes to amplifier 48, and from there to antenna 49 as in the embodiment of FIG. 1. Depending upon which of outputs 36 or 37 is energized, oscillator 57 will be caused to emit a burst of RF energy at the appropriate corresponding frequency, so that the overall operation is the same as the embodiment in FIG. 1.

In the event of pulse coincidence, controller 50 will suppress the later starting coincident pulse and simultaneously delay its corresponding rate generator for a preset time interval. For the purpose of explaining one possible anti-coincidence operative mode of controller 50, assume the channel 2 rate generator 43 and pulse shaper 44 are generating the channel 2 waveforms indicated in FIG. 2. Further assume that channel 1 pulse shaper 41 has attempted to deliver to controller 50 input 32 the coincident (with the channel 2 pulse) pulse shown in FIG. 2 (labeled conductor 11, input 32) as occurring at time $t_2$.

Figures 3, 5:
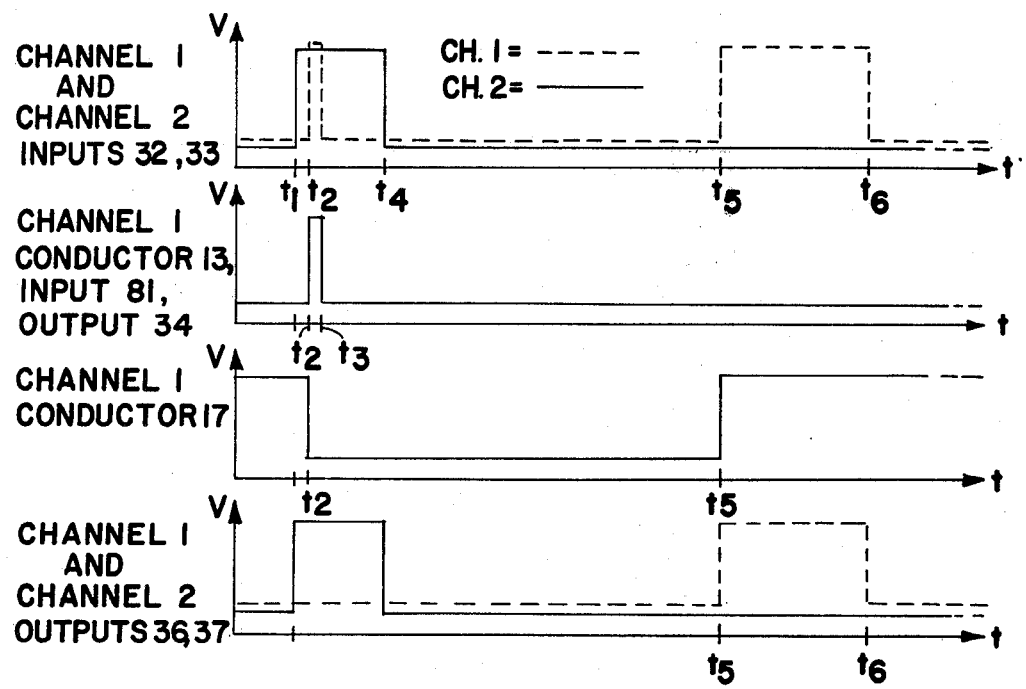
FIG. 5 is a logic table for a D-type flip-flop.

As illustrated, the channel 1 pulse is initiated on conductor 11 and subsequently input 32 of controller 50 at time $t_2$ after the beginning but before the end of the channel 2 pulse occurring during the time interval $t_1$ to $t_4$ on input 33 of controller 50. FIG. 3 shows a composite of these two pulses in a graph appropriately labeled Channel 1 and Channel 2 inputs 32, 33. It will be observed that the time scales of the graphs in FIG. 3 are exaggerated so that the timing relationship of the pulses there illustrated may be better seen. Also depicted in FIG. 3 and so indicated are the composite waveforms of controller 50 outputs 37 and 36 which correspond to channel 2 and channel 1, respectively. As illustrated, the channel 2 pulse at time $t_1$ is passed by controller 50. The channel 1 pulse does not pass but instead triggers the channel 1 time delay 42 via the pulse occurring on controller 50 delay output 34 at time $t_2$. This trigger pulse is delivered to time delay 42 input 81 through conductor 13 and is so represented in FIG. 3 in the graph correspondingly labeled.

Being so triggered, channel 1 time delay 42 outputs into conductor 17 and consequently the gate of VFET 61 the low voltage pulse indicated in the corresponding FIG. 3 graph. By referring back to FIG. 2 it will be seen that the voltage on node 21 follows the voltage level of conductor 17 during the time interval $t_2$ to $t_5$, which is the preset delay interval of time delay 42.

The voltage on node 21 being so altered switches Schmitt trigger inverter 69 such that its output voltage occurring on conductor 19 pulls up the voltage on node 24 of pulse shaper 41 and consequently terminates at time $t_3$ the channel 1 pulse present on conductor 11 and input 32 of controller 50. The sequence and relationship of these events can be seen by examining the bottom three graphs of FIG. 2.

For the purpose of clarification note that the channel 1 pulse occurring at time $t_2$ is truncated at time $t_3$ by the action of controller 50 and time delay 42, and had it been non-coincident with the channel 2 pulse, it would have appeared as it does during the time interval $t_5$ to $t_6$ and so illustrated by the appropriate graphs of FIG. 2 and FIG. 3. Also note that the pulse width of the truncated channel pulse is exaggerated in relation to the time scale in order to more clearly illustrate the operation of the controller-transmitter unit. In reality, truncation occurs within microseconds of coincidence so that the truncated pulse appears only as a voltage spike on the input of the controller.

At time $t_5$ or the end of the preset delay of time delay 42, channel 1 rate generator 40 returns to its free running mode. By virtue of the characteristics of VFET 61, node 22 (the drain of VFET 61) is isolated from the gate and source voltage during the delay interval and consequently capacitor 63 is amply charged at the end of said delay interval to cause the immediate reinitiation of the delayed channel 1 pulse when VFET 61 returns to its "on" condition. This is an important feature in that it permits the rate generator to be suspended in defined state and thereby allowing accurate staggering of the delayed pulse. Another important feature is the 2 millisecond preset delay time interval of the time delays. In that capacitor 63 charges through adjustable resistor 65 during the suspended interval of the channel 1 rate generator 40, charge in excess of that required to switch Schmitt trigger inverter 68 accumulates on capacitor 63. Remembering that this excess charge must be dissipated in the discharge cycle of the rate generator, it will be seen that it has the effect of lengthening the rate period and therefore must be minimized by choosing a short delay in order to maintain a uniform rate period. Another criterion for choosing the 2 millisecond delay time pertains to the necessity of staggering the delayed pulse between the pulses of the alternate channel. Given a typical pulse period of 30 milliseconds and a typical pulse width of 0.2 milliseconds, it will be seen that the 2 millisecond delay properly staggers the delayed pulse for a wide range of pulse rates and widths. Still another purpose for the 2 millisecond preset delay is to provide the tuned circuits in the output network ample time to dissipate stored charge before re-energization.

Figure 4:
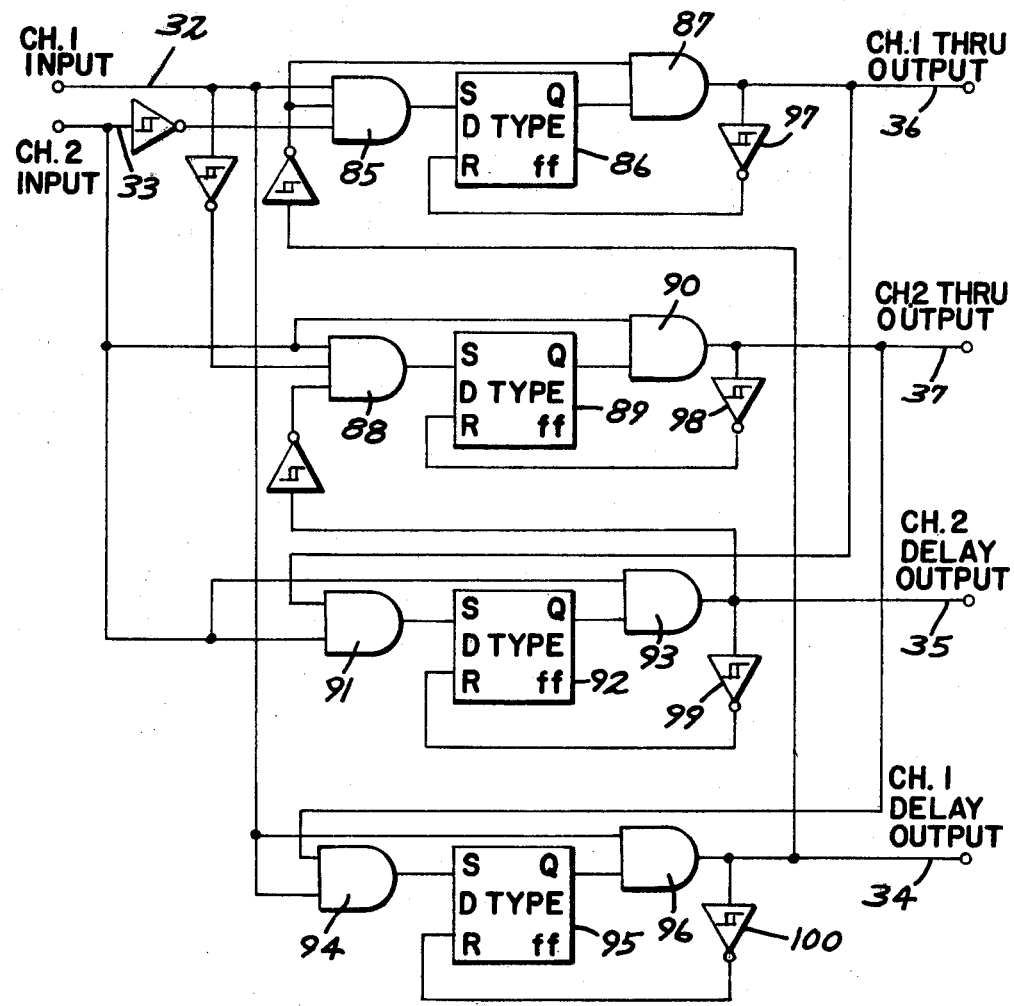
FIG. 4 is an electrical schematic diagram of the dual independent rate controller of FIG. 1.

Before explaining the function of controller 50 in the previously discussed example a brief overview of its configuration is appropriate. FIG. 4 is an electrical schematic diagram of controller 50. It is designed with only three different component types: (1) AND gates; (2) Schmitt trigger inverters; and (3) D-type flip-flops. The unique logic of the D-type flip-flop (shown in FIG. 5) is important to the operation of the embodiment of the invention as configured in FIG. 4.

Controller 50 has four principal paths of signal flow, two "pass" paths and two "delay" paths, one path of each type associated with each channel. Channel 1 "pass" paths traverses AND gate 85, flip-flop 86, and AND gate 87 in going from input 32 to thru output 36. The channel 2 "pass" path similarly traverses the corresponding elements 88, 89, and 90 in going from input 33 to thru output 37. The channel 1 "delay" path leads from input 32 to delay output 34 via AND gate 94, flip-flop 95, and AND gate 96 while the channel 2 "delay" path traverses the corresponding elements 91, 92, and 93 in going from input 33 to delay output 35.

Returning to the example, it was so noted above that the channel 2 pulse occurring at time $t_1$ is passed by controller 50. With regard to FIG. 4, the channel 2 pulse propagates through controller 50 to channel 2's thru output 37 via elements 88, 89, and 90. In addition, the channel 2 pulse is inverted and applied to one input of AND gate 85, thereby preventing the propagation of the channel 1 pulse through controller 50 for the duration of the channel 2 pulse. The occurrence of the channel 1 pulse on input 11 at time $t_2$ does two things; (1) it disables AND gate 88; and (2) it activates the channel 1 delay output 34 via elements 94, 95, and 96. Even though AND gate 88 is thus disabled, the channel 2 pulse continues to propagate through controller 50 because flip-flop 89 remains set for the duration of the channel 2 pulse. In a similar manner, flip-flop 95 will prevent any portion of the truncated channel 1 pulse in the unlikely circumstance that it persists after the channel 2 pulse ends, from propagating through controller 50 and energizing the associated RF oscillator prematurely. In essence, it provides the means for keeping AND gate 85 disabled for any duration of the channel 1 pulse that occurs after the channel 2 pulse has dropped out. Because flip-flop 95 and its corresponding flip-flop 92 are utilized only in this unlikely circumstance the circuit of controller 50 could be simplified by their elimination.

The return of controller 50 to its quiescent or reset mode occurs when both of its inputs reassume a low level voltage. This return to a reset mode is accomplished with Schmitt triggers 97, 98, 99, and 100 all of which serve to reset the respective flip-flops 86, 89, 92, and 95.

While only VCC 74 is depicted in the electrical drawings, it will be understood that the usual connections for power are provided for the various circuit components.

It will be seen from the foregoing that the present invention prevents delivery of coincident or overlapping stimulation pulses to the output amplifier of the transmitter, thus avoiding the undesirable result of transmitting undefined stimulation pulses to the receiver implanted in the patient. More importantly, it will be seen that the present invention provides the for allowing the output amplifier sufficient time to fully dissipate stored charge before the initiation of a subsequent stimulation pulse, while preserving the integrity of pulse rate and width.

What is claimed is:

1. An independently rate-adjustable multiple channel controller-transmitter for a nerve stimulator to be used in conjunction with an implanted stimulation pulse output unit comprising:

rate generating means for producing a plurality of trigger signals of independently adjustable rate;

transmitting means for generating pulsed bursts of RF energy at separate frequencies for each of said channels, in response to the corresponding trigger signals of said rate generating means, to be received by said implanted unit; and means operatively connected for normally passing said trigger signals from said rate generating means to said transmitting means and operative upon coincidence of said trigger signals for preventing the overlap of said trigger signals in said transmitting means.

2. An independently rate adjustable multiple channel controller-transmitter according to claim 1 wherein said rate generating means includes means for adjusting trigger signal width for controlling the pulse width of said bursts of RF energy.

3. An independently rate adjustable multiple channel controller-transmitter according to claim 1 wherein said transmitting means includes an oscillator having selectable tuning components switchable in response to trigger signals corresponding to the respective multiple channels to produce said pulsed bursts of RF energy at the corresponding frequency for the respective multiple channels.

4. An independently rate-adjustable dual channel controller-transmitter for a nerve stimulator to be used in conjunction with an implanted stimulation pulse output unit comprising:
first and second rate generating means for producing trigger signals of independently adjustable rate for each of said dual channels;
transmitting means for generating pulsed bursts of RF energy at first and second frequencies, in response to the corresponding trigger signals of said first and second rate generating means, to be received by said implanted unit; and
means operatively connected for normally passing trigger signals from said first and second rate generating means to said transmitting means and operative upon overlap of said trigger signals from said first and second rate generating means for preventing the overlap of said trigger signals in said transmitting means.

5. An independently rate-adjustable dual channel controller-transmitter according to claim 4 wherein said rate generating means includes means for adjusting trigger signal width for controlling the pulse width of said bursts of RF energy.

6. An independently rate adjustable dual channel controller-transmitter according to claim 4 wherein said transmitting means includes an oscillator having selectable tuning components switchable in response to trigger signals corresponding to the respective dual channels to produce said pulsed bursts of RF energy at the corresponding frequency for the respective channels.

7. An independently rate-adjustable dual channel controller-transmitter for a nerve stimulator to be used in conjunction with an implanted stimulation pulse output unit comprising:
first and second rate generating means for producing trigger signals of independently adjustable rate;
transmitting means for generating pulse bursts of RF energy at first and second frequencies, in response to the corresponding trigger signals of said first and second rate generating means, to be received by said implanted unit; and
anti-overlap means operatively connected for normally passing trigger signals from said first and second rate generating means to said transmitting means and including means operative upon overlap of trigger signals from said first and second rate generating means for blocking and delaying the later starting of said overlapping trigger signals for preventing the overlap of said trigger signals for said transmitting means.

8. An independently rate adjustable dual channel controller-transmitter according to claim 7 wherein said rate generating means includes means for adjusting trigger signal width for controlling the pulse width of said bursts of RF energy.

9. An independently rate adjustable dual channel controller-transmitter according to claim 7 wherein said transmitting means includes an oscillator having selectable tuning components switchable in response to trigger signals corresponding to the respective dual channels to produce said pulsed bursts of RF energy at the corresponding frequency for the respective channels.

10. An independently rate-adjustable dual channel controller-transmitter for a nerve stimulator to be used in conjunction with an implanted stimulation pulse output unit comprising:
first and second rate generating means for producing trigger signals of independently adjustable rate;
transmitting means for generating pulse bursts of RF energy at first and second frequencies, in response to the corresponding trigger signals of said first and second rate generating means, to be received by said implanted unit;
first and second delay means operatively connected to the respective first and second rate generating means for selectively suspending operation of either said first or second rate generating means; and
anti-overlap means operatively connected for normally passing trigger signals from said first and second rate generating means to said transmitting means and operative upon any overlap of said trigger signals from said first and second rate generating means for preventing the overlap of said trigger signals in said transmitting means by activating the delay means corresponding to the later occurring trigger signal.

11. An independently rate adjustable dual channel controller-transmitter according to claim 10 wherein said delay means includes a VFET operative as a switch for suspending operation of said rate generating means.

12. An independently rate adjustable dual channel controller-transmitter according to claim 10 wherein each of said rate generating means includes an adjustable RC charging circuit, a Schmitt trigger inverter, and a VFET operatively connected as a switch between the output of said adjustable RC charging circuit and the input of said Schmitt trigger inverter, the VFET connected for control by the respective one of said delay means.

13. An independently rate adjustable dual channel controller-transmitter according to claim 10 wherein said rate generating means includes means for adjusting trigger signal width for controlling the pulse width of said bursts of RF energy.

14. An independently rate adjustable dual channel controller-transmitter according to claim 10 wherein said transmitting means includes an oscillator having selectable tuning components switchable in response to trigger signals corresponding to the respective dual channels to produce said pulsed bursts of RF energy at the corresponding frequency for the respective channels.

15. An independently rate-adjustable dual channel controller-transmitter for a nerve stimulator to be used in conjunction with an implanted stimulation pulse output unit comprising:
first and second rate generating means for producing rate trigger signals of independently adjustable rate;

first and second pulse shaping means operatively connected to said first and second rate generating means respectively for generating pulse trigger signals of adjustable width in response to rate trigger signals from said first and second rate generating means;

transmitting means for generating pulsed bursts of RF energy at first and second frequencies, in response to the corresponding pulse trigger signals of said first and second pulse shaping means, to be received by said implanted unit;

anti-overlap means connected to said first and second pulse shaping means, said transmitting means, and said first and second rate generating means, and operative to normally pass pulse trigger signals from said first and second pulse shaping means to said transmitting means, and to prevent overlap of said pulse trigger signals in said transmitting means, by blocking the later occurring one of overlapping pulse trigger signals;

first and second delay timing means operatively connected between said anti-overlap means and the respective said first and second rate generating means and independently activated by said anti-overlap means for producing first and second delay switching signals; and first and second switching means operatively connected within the respective said first and second rate generating means for selectively holding said first and second rate generating means in a defined OFF condition in response to one of said first and second delay switching signals.

16. An independently rate adjustable dual channel controller-transmitter according to claim 15 wherein said switching means comprises a VFET operatively connected as a switch for suspending operation of said rate generating means.

17. An independently rate adjustable dual channel controller-transmitter according to claim 15 wherein each of said rate generating means includes an adjustable RC charging circuit, a Schmitt trigger inverter, and a VFET operatively connected as a switch between the output of said adjustable RC charging circuit and the input of said Schmitt trigger inverter, the VFET connected for control by the respective one of said delay means.

* * * * *